(12) United States Patent
Liu et al.

(10) Patent No.: US 10,130,307 B2
(45) Date of Patent: Nov. 20, 2018

(54) ELECTROCARDIOGRAM (ECG) AUTHENTICATION METHOD AND APPARATUS

(71) Applicant: SAMSUNG ELECTRONICS CO., LTD., Suwon-si (KR)

(72) Inventors: Yang Liu, Beijing (CN); Xuetao Feng, Beijing (CN); Chao Zhang, Beijing (CN); Chisung Bae, Yongin-si (KR); Sang-joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/371,454

(22) Filed: Dec. 7, 2016

(65) Prior Publication Data

US 2017/0188971 A1 Jul. 6, 2017

(30) Foreign Application Priority Data

Jan. 6, 2016 (CN) .......................... 2016 1 0007772
Sep. 19, 2016 (KR) ........................ 10-2016-0119392

(51) Int. Cl.
| | | |
|---|---|---|
| *A61B 5/04* | (2006.01) | |
| *A61B 5/00* | (2006.01) | |
| *A61B 5/044* | (2006.01) | |
| *A61B 5/0452* | (2006.01) | |
| *A61B 5/117* | (2016.01) | |

(52) U.S. Cl.
CPC .......... *A61B 5/7264* (2013.01); *A61B 5/0006* (2013.01); *A61B 5/044* (2013.01); *A61B 5/04017* (2013.01); *A61B 5/04525* (2013.01); *A61B 5/117* (2013.01); *A61B 5/681* (2013.01); *A61B 5/7267* (2013.01)

(58) Field of Classification Search
CPC ... A61B 5/0006; A61B 5/04017; A61B 5/044; A61B 5/04525; A61B 5/117; A61B 5/681; A61B 5/7264; A61B 5/7267
See application file for complete search history.

(56) References Cited

U.S. PATENT DOCUMENTS 7,630,521 B2 * 12/2009 Kim .................... G06K 9/00496
382/115
2005/0171451 A1 8/2005 Yeo et al.
(Continued)

FOREIGN PATENT DOCUMENTS

| JP | 2006-218033 A | 8/2006 |
|---|---|---|
| JP | 2012-176106 A | 9/2012 |

(Continued)

OTHER PUBLICATIONS

R. Palaniappan, et al., "Identifying Individuals Using ECG Beats," *Proceedings from the International Conference on Signal Processing & Communications*, SPCOM, Dec. 2004, pp. 569-572.
(Continued)

*Primary Examiner* — George Manuel
(74) *Attorney, Agent, or Firm* — NSIP Law

(57) ABSTRACT

Disclosed are an electrocardiogram (ECG) authentication method and apparatus, and a training method and apparatus for training a neural network model used for ECG authentication, the ECG authentication apparatus being configured to acquire an ECG signal of a subject, extract a semantic feature of the ECG signal, and authenticate the subject based on the extracted semantic feature.

20 Claims, 18 Drawing Sheets

(56) References Cited

U.S. PATENT DOCUMENTS

| | | | |
|---|---|---|---|
| 2008/0033313 A1 | 2/2008 | Couderc et al. | |
| 2011/0224526 A1 | 9/2011 | Garcia Alberola et al. | |
| 2013/0112557 A1* | 5/2013 | Javitt | A61B 5/14532 204/403.01 |
| 2014/0188770 A1* | 7/2014 | Agrafioti | A61B 5/117 706/13 |
| 2015/0028996 A1 | 1/2015 | Agrafioti et al. | |

FOREIGN PATENT DOCUMENTS

| | | |
|---|---|---|
| JP | 2014-530057 A | 11/2014 |
| KR | 10-2011-0096473 A | 8/2011 |
| KR | 10-2015-0068694 A | 6/2015 |
| WO | WO 2005/058160 A1 | 6/2005 |

OTHER PUBLICATIONS

Y. Wan, et al., "A Neural Network to Identify Human Subjects with Electrocardiogram Signals," *Proceedings of the World Congress on Engineering and Computer Science*, WCECS 2008, Oct. 2008, San Francisco, CA, USA (4 pages, in English).

A. Page, et al., "Utilizing Deep Neural Nets for an Embedded ECG-based Biometric Authentication System," *Proceedings of the IEEE Biomedical Circuits and Systems Conference*, Oct. 2015 (4 pages, in English).

Partial European Search Report dated May 16, 2017, in corresponding European Application No. 16207565.9 (17 pages, in English).

\* cited by examiner

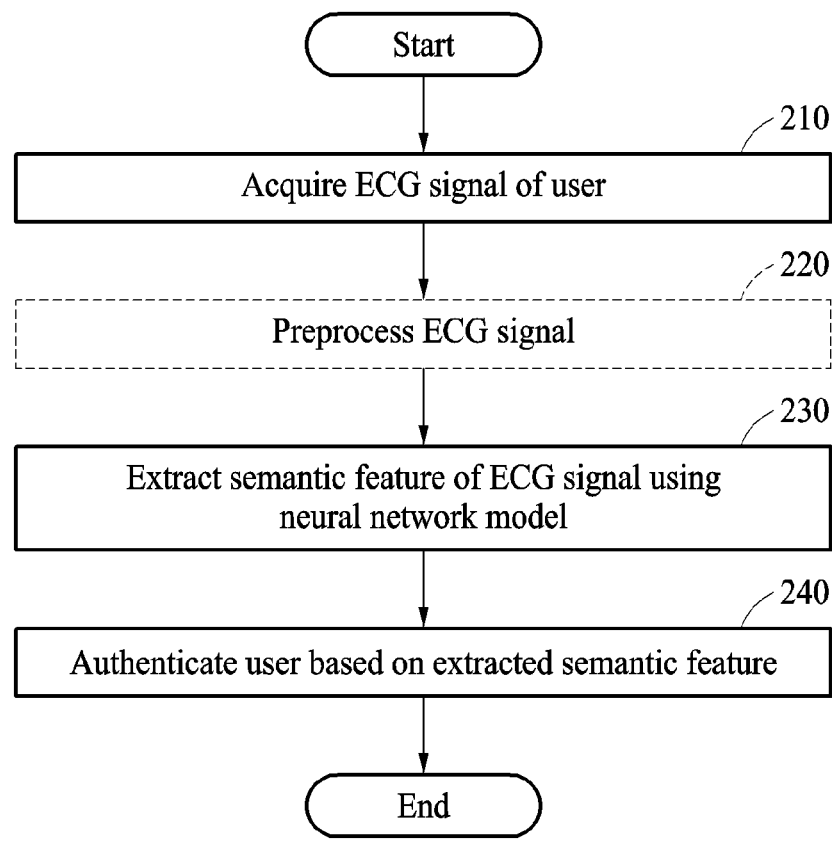

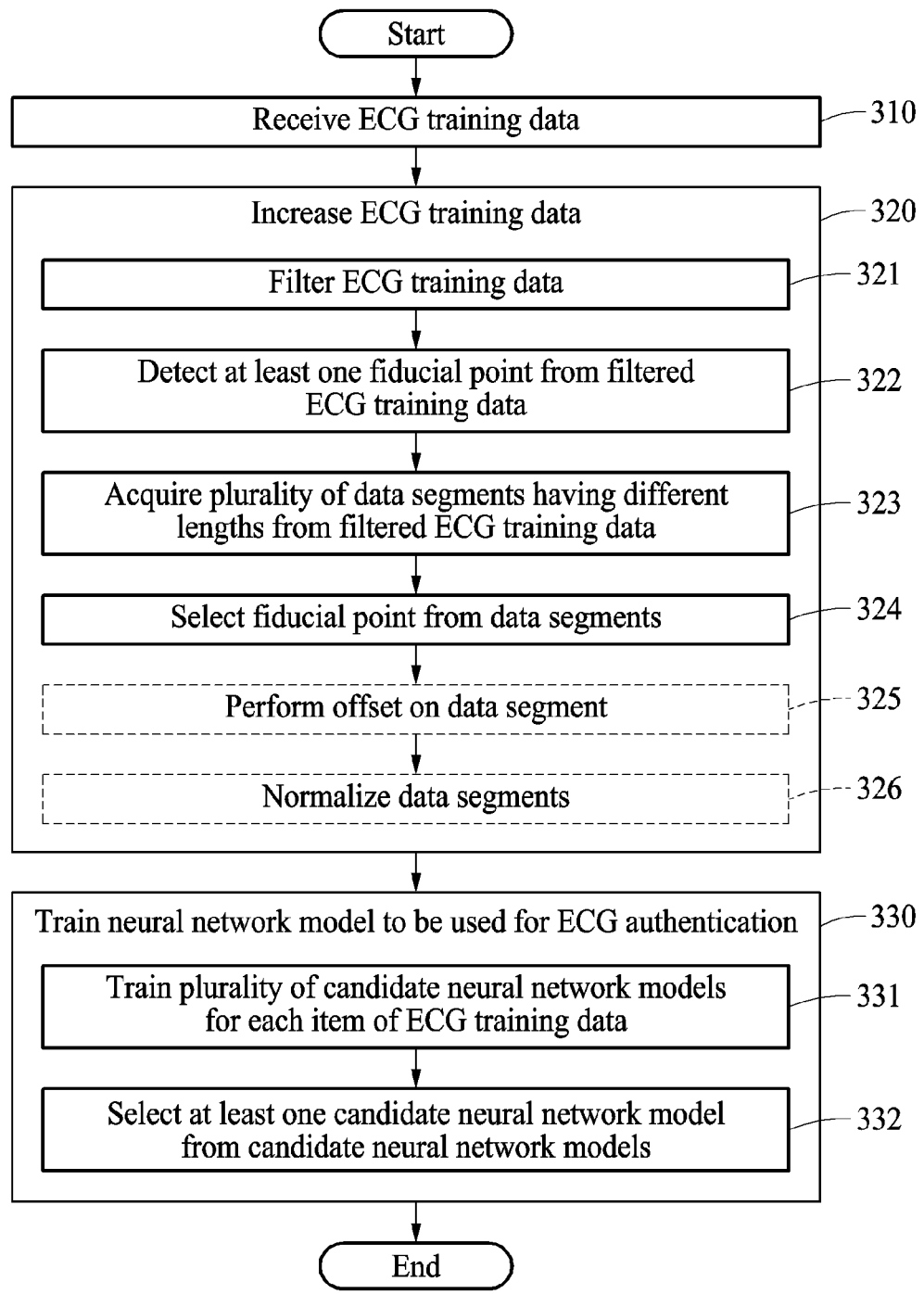

1-30 hz 3-30 hz

R:L=30

R:L=50

L=60

Reference L=155

ELECTROCARDIOGRAM (ECG) AUTHENTICATION METHOD AND APPARATUS

CROSS-REFERENCE TO RELATED APPLICATION(S)

This application claims the benefit under 35 USC § 119(a) of Chinese Patent Application No. 201610007772.7 filed on Jan. 6, 2016, in the State Intellectual Property Office of the People's Republic of China and Korean Patent Application No. 10-2016-0119392 filed on Sep. 19, 2016 in the Korean Intellectual Property Office, the entire disclosures of which are incorporated herein by reference for all purposes.

BACKGROUND

1. Field

The following description relates to biometric authentication technology for authenticating a user based on a biosignal.

2. Description of Related Art

Biometric authentication is technology for identifying a user based on individual biological or behavior feature such as, for example, an iris, a fingerprint, a pulse pattern, a gait. In biometric authentication, an electrocardiogram (ECG) authentication is a method of identifying a user based on an ECG signal. Because these unique biosignals are not easily stolen or accidentally lost and are robust against forgery or falsification, the application of the ECG authentication in security technology is promising.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an electrocardiogram (ECG) authentication method including acquiring an ECG signal of a subject, extracting a semantic feature of the acquired ECG signal using a neural network model, and authenticating the subject based on the extracted semantic feature.

The ECG authentication method may include preprocessing the ECG signal before extracting the semantic feature, wherein the preprocessing includes filtering the acquired ECG signal, detecting at least one fiducial point from the filtered ECG signal based on a fiducial point corresponding to the neural network model, and acquiring a data segment from the filtered ECG signal based on the at least one fiducial point.

The extracting of the semantic feature of the ECG signal may include extracting a semantic feature from the data segment using the neural network model.

The at least one fiducial point may include a peak point of the filtered ECG signal and a minimum point close to the peak point.

The authenticating may include calculating a similarity between the extracted semantic feature and a registered feature, and determining an authentication of the ECG signal based on a comparison of the similarity and a threshold.

The neural network model may be a semantic feature extraction model trained using a deep learning scheme based on ECG training data.

The at least one fiducial point may include at least one of: the peak point of the filtered ECG signal and a left and a right minimum points close to the peak point, the peak point and the left minimum point, or the peak point and the right minimum point.

In another general aspect, there is provided an electrocardiogram (ECG) authentication apparatus including a processor configured to receive an ECG signal of a subject, extract a semantic feature of the ECG signal using a neural network model, and authenticate the subject based on the extracted semantic feature.

In one general aspect, there is provided a training method including receiving electrocardiogram (ECG) training data, augmenting the ECG data, and training a neural network model for ECG authentication based on the augmented ECG training data.

The augmenting of the ECG data may include filtering the ECG training data using a filter, detecting at least one fiducial point from the filtered ECG training data, and acquiring a plurality of data segments having different lengths from the filtered ECG training data based on the at least one fiducial point.

The filtering of the ECG training data may include filtering the ECG training data using a band pass filter having different passbands.

The filtering of the ECG training data may include filtering the ECG training data using a band pass filter having a fixed passband.

The at least one fiducial point may include a peak point of the filtered ECG training data and a minimum point close to the peak point.

The augmenting of the ECG training data may include selecting a fiducial point from a current data segment of the ECG training data, performing an offset on the current data segment based on the fiducial point, and normalizing a data segment obtained through the offset.

The training of the neural network model may include training a plurality of candidate neural network models for each item of the augmented ECG training data, and selecting at least one candidate neural network model from the candidate neural network models based on an accuracy of a candidate semantic feature extracted using each of the candidate neural network model.

A final neural network model used for the ECG authentication may be determined based on the selected at least one candidate neural network model.

The training method may include selecting a second candidate neural network model from the remaining candidate neural network models to increases the accuracy based on the semantic feature corresponding to the second candidate neural network model being combined with the selected candidate semantic feature.

The training of the neural network model may include training the neural network model based on an identification signal for identifying an entity corresponding to the ECG training data and an authentication signal for verifying whether items of ECG training data corresponds to the same entity.

In another general aspect, there is provided electrocardiogram (ECG) authentication device including an antenna, a cellular radio configured to transmit and receive data via the antenna according to a cellular communications standard, a touch-sensitive display, a sensor configured to measure an ECG signal of a subject, a memory configured to store instructions, and a processor configured to receive the ECG signal, to extract a semantic feature of the ECG signal using a neural network model, to authenticate the subject based on the extracted semantic feature, and to display the result of the authenticate on the touch-sensitive display.

The processor may receive the ECG signal, measured by another device, using the antenna.

Other features and aspects will be apparent from the following detailed description, the drawings, and the claims.

BRIEF DESCRIPTION OF THE DRAWINGS

FIG. 2 illustrates an example of an operation of an ECG authentication method.

FIG. 3 illustrates an example of training a neural network model based on ECG training data.

Figure 1:
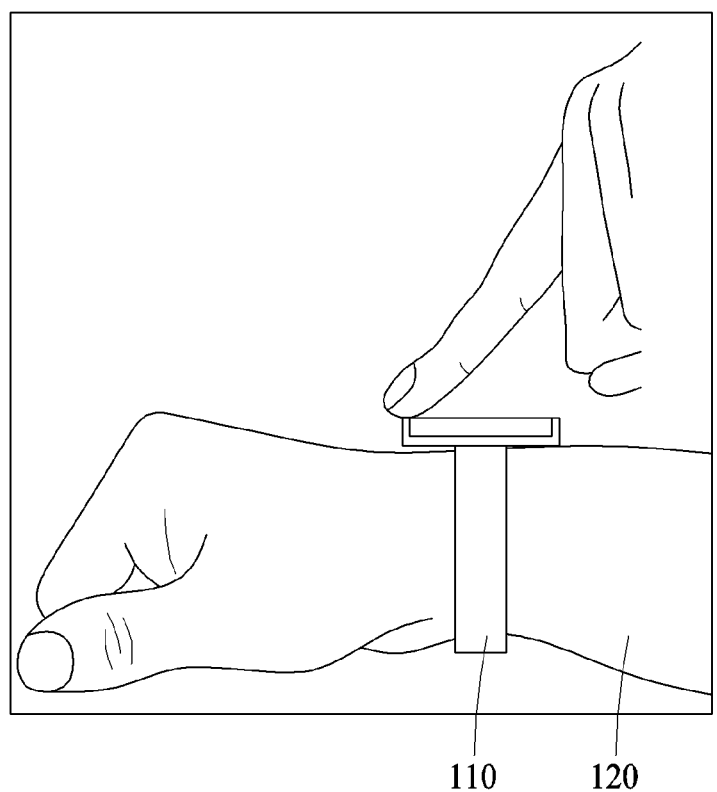
FIG. 1 illustrates an example of authenticating a user based on an electrocardiogram (ECG) signal.
Figure 4A:
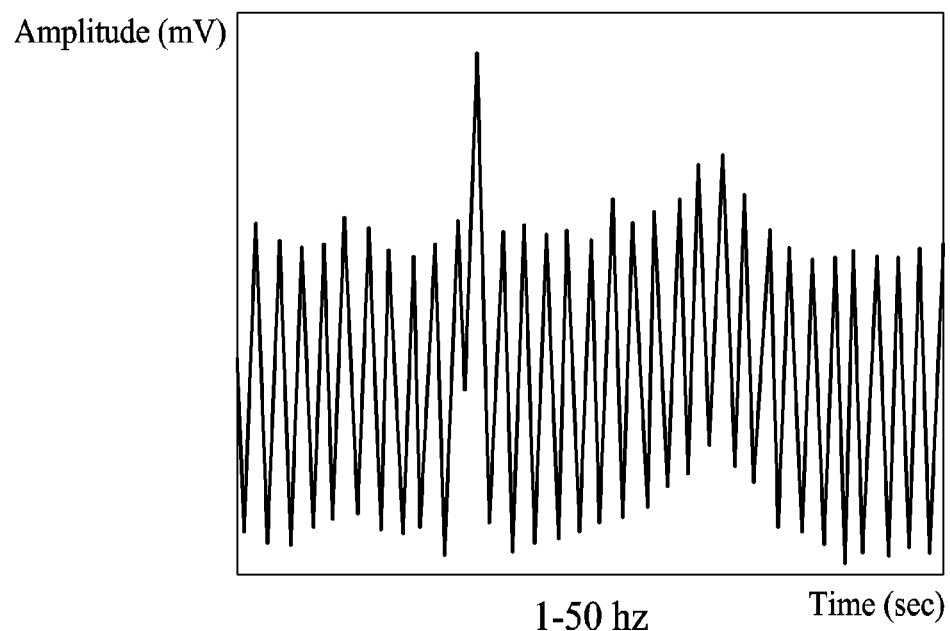
FIGS. 4A through 4E illustrate examples of a filtering result of ECG training data.
Figure 4B:
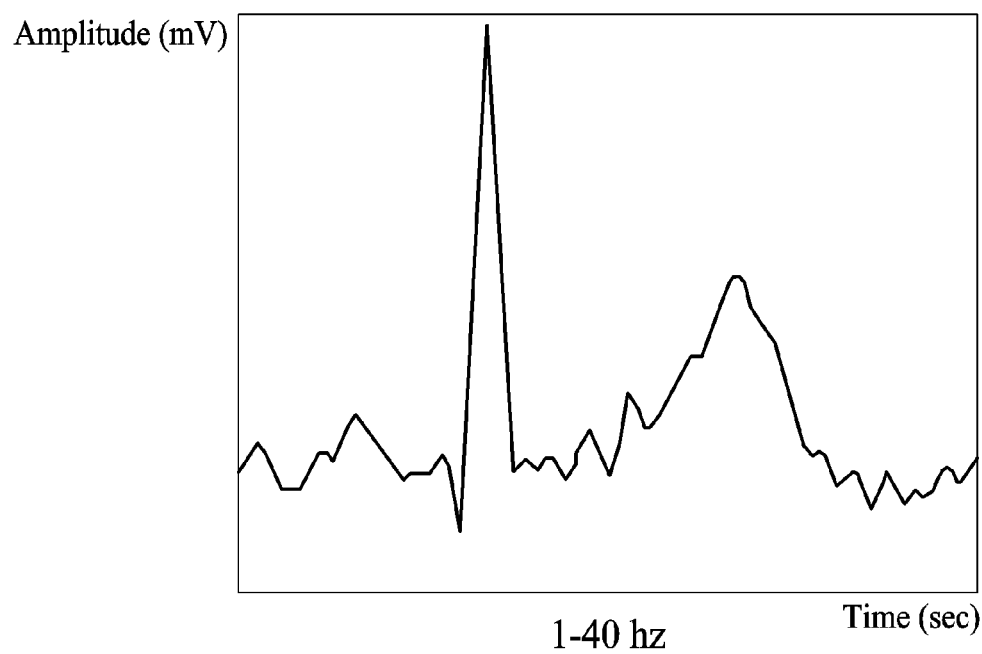
Figure 4C:
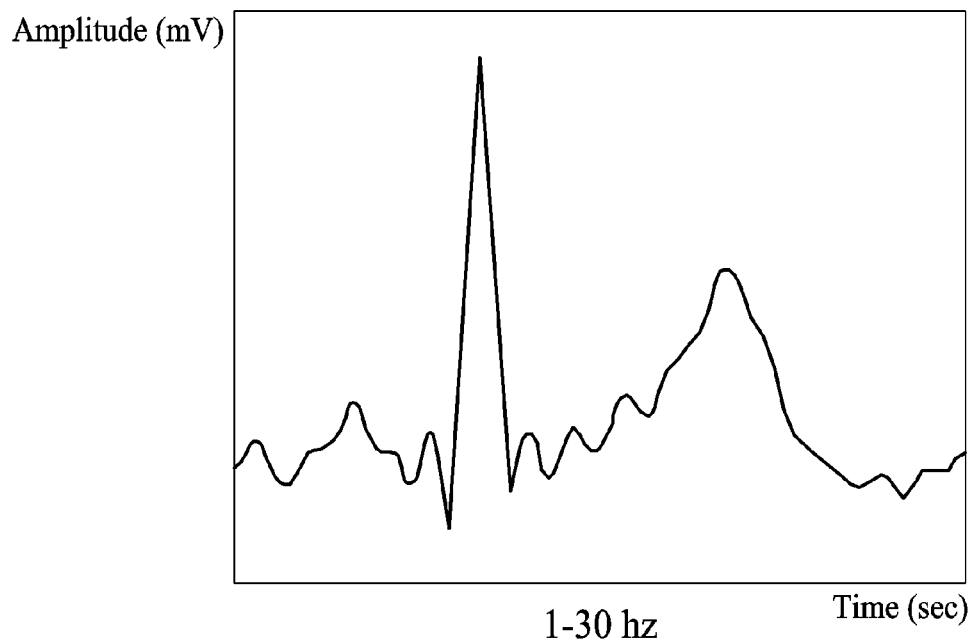
Figure 4D:
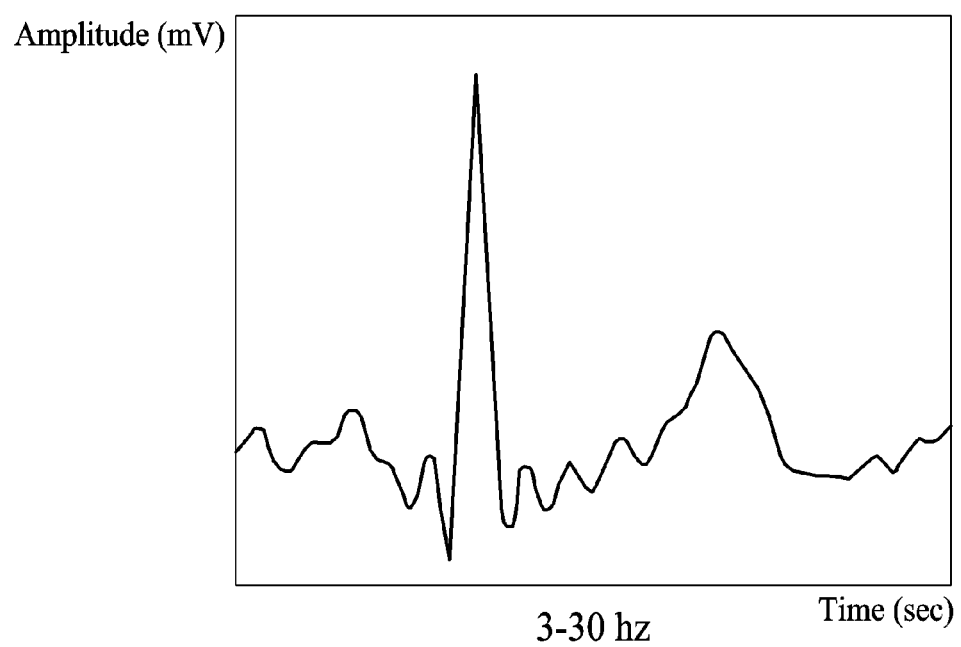
Figure 4E:
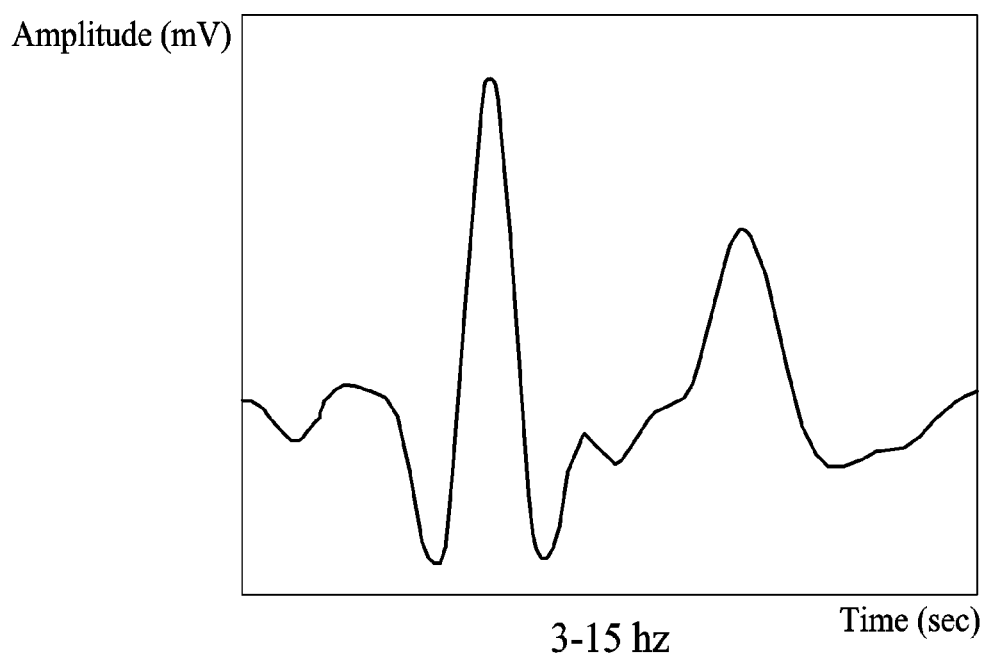

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or apparatuses described herein. However, various changes, modifications, and equivalents of the methods, apparatuses, and/or apparatuses described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or apparatuses described herein that will be apparent after an understanding of the disclosure of this application.

Various alterations and modifications may be made to the examples. Here, the examples are not construed as limited to the disclosure and should be understood to include all changes, equivalents, and replacements within the idea and the technical scope of the disclosure.

Terms such as first, second, A, B, (a), (b), and the like may be used herein to describe components. Each of these terminologies is not used to define an essence, order or sequence of a corresponding component but used merely to distinguish the corresponding component from other component(s). For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular examples only, and is not to be used to limit the disclosure. As used herein, the terms "a," "an," and "the" are intended to include the plural forms as well, unless the context clearly indicates otherwise. As used herein, the terms "include, "comprise," and "have" specify the presence of stated features, numbers, operations, elements, components, and/or combinations thereof, but do not preclude the presence or addition of one or more other features, numbers, operations, elements, components, and/or combinations thereof.

FIG. 1 illustrates an example of authenticating a user based on an electrocardiogram (ECG) signal.

An ECG authentication apparatus 110 performs ECG authentication based on an ECG signal of a user 120. An ECG signal is a signal including information on an electrical activity of a heart. In an example, the ECG signal is measured by contacting electrodes included in the ECG authentication apparatus 110 to a skin of the user 120. An ECG authentication includes a process of determining whether the user 120 is a preregistered user based on an ECG signal measured from a body of the user 120. The ECG authentication is applicable to various applications such as, for example, an access control, financial transactions, a check-in at an airport, a health care service, and a security service.

In an example of FIG. 1, the ECG authentication apparatus 110 may be embedded in or interoperate with various digital devices such as, for example, a mobile phone, a cellular phone, a smart phone, a personal computer (PC), a laptop, a notebook, a subnotebook, a netbook, or an ultra-mobile PC (UMPC), a tablet personal computer (tablet), a phablet, a mobile internet device (MID), a personal digital assistant (PDA), an enterprise digital assistant (EDA), a digital camera, a digital video camera, a portable game console, an MP3 player, a portable/personal multimedia player (PMP), a handheld e-book, an ultra mobile personal computer (UMPC), a portable lab-top PC, a global positioning system (GPS) navigation, a personal navigation device or portable navigation device (PND), a handheld game console, an e-book, and devices such as a high definition television (HDTV), an optical disc player, a DVD player, a Blue-ray player, a setup box, robot cleaners, a home appliance, content players, communication systems, image processing systems, graphics processing systems, other consumer electronics/information technology (CE/IT) device, or any other device capable of wireless communication or network communication consistent with that disclosed herein. The ECG authentication apparatus 110 may be embedded in or interoperate with a smart appliance, an intelligent vehicle, an apparatus for automatic driving, a smart home environment, a smart building environment, a smart office environment, office automation, and a smart electronic secretary system.

The digital devices may also be implemented as a wearable device, which is worn on a body of a user. In one example, a wearable device may be self-mountable on the body of the user, such as, for example, a ring, a watch, a pair of glasses, glasses-type device, a bracelet, an ankle bracket, a belt, a band, an anklet, a belt necklace, an earring, a headband, a helmet, a device embedded in the cloths, or as an eye glass display (EGD), which includes one-eyed glass or two-eyed glasses. In another non-exhaustive example, the wearable device may be mounted on the body of the user through an attaching device, such as, for example, attaching a smart phone or a tablet to the arm of a user using an armband, incorporating the wearable device in a cloth of the user, or hanging the wearable device around the neck of a user using a lanyard. In an example, when the user 120 wearing the wearable device on one hand contacts one of the electrodes in the wearable device using another hand, an electric closed circuit may be formed in the body of the user 120. In such electric closed circuit, a change in current due to a heartbeat may be measured as a change in ECG.

The ECG authentication apparatus 110 extracts a feature of an ECG signal acquired using a neural network model and determines whether to authenticate based on the extracted feature. For example, the ECG authentication apparatus 110 calculates a similarity between the extracted feature and a preregistered feature. In this example, the ECG authentication apparatus 110 determines that an authentication succeeds when the similarity is greater than or equal to a threshold, and determines that the authentication fails when the similarity is less than the threshold. The neural network model is a statistical model obtained through an imitation of a biological neural network and acquires a problem-solving skill through a training process. Parameters of the neural network model are adjusted through the training process.

The ECG authentication apparatus 110 acquires the feature of the ECG signal representing a unique biometric feature of the user 120 using the neural network trained based on various training data. The feature of the ECG signal acquired by the ECG authentication apparatus 110 is a feature acquired using the trained neural network model. The feature is also referred to as, for example, semantic feature.

FIG. 2 illustrates an example of a method of ECG authentication. The operations in FIG. 2 may be performed in the sequence and manner as shown, although the order of some operations may be changed or some of the operations omitted without departing from the spirit and scope of the illustrative examples described. Many of the operations shown in FIG. 2 may be performed in parallel or concurrently. In addition to the description of FIG. 2 below, the above descriptions of FIG. 1, are also applicable to FIG. 2, and are incorporated herein by reference. Thus, the above description may not be repeated here.

Referring to FIG. 2, in 210, an ECG authentication apparatus, for example, the ECG authentication apparatus 110 of FIG. 1 or an ECG authentication apparatus 1000 acquires an ECG signal of a user. For example, the ECG authentication apparatus acquires the ECG signal using a sensor included in the ECG authentication apparatus or receives an ECG signal measured by another device.

In 220, the ECG authentication apparatus preprocesses the ECG signal. The preprocessing includes detection of a fiducial point and acquisition of a data segment. For example, the ECG authentication apparatus filters the ECG signal using a band pass filter configured to pass a predefined frequency band. A characteristic of a passing frequency band of the band pass filter is determined in a process of training a neural network model used for extracting a semantic feature of the ECG. Through filtering, noise included in the ECG signal is removed or an ECG signal corresponding to a frequency band of interest is acquired from the ECG signal.

The ECG authentication apparatus detects at least one fiducial point from the filtered ECG signal. The fiducial point includes at least one of a peak point and at least one minimum point close to the peak point. The fiducial point is also referred to as a key point. The ECG signal has a plurality of maximum points and minimum points. Minimum points close to the peak point are defined based on the peak point among the maximum points and minimum points. A fiducial point to be detected from the filtered ECG signal is previously determined in a process of training the neural network model. For example, a type of the fiducial point to be detected is previously determined by detecting the peak point or detecting the minimum point close to the peak point from the filtered ECG signal. When a plurality of fiducial points is used, accuracy on identification may increase.

The ECG authentication apparatus acquires a data segment from the filtered ECG signal based on the detected fiducial point. For example, the ECG authentication apparatus acquires a signal having a length previously defined based on the peak point in the filtered ECG signal as the data segment. In this example, the length previously defined based on the peak point may be a predefined time interval measured before and after the peak point.

Depending on an example, the preprocessing may not be performed in some cases.

In 230, the ECG authentication apparatus extracts the semantic feature of the ECG signal using the neural network model. The neural network model is a feature extracting model previously trained based on training data. The neural network data outputs the semantic feature of the ECG signal used for ECG authentication based on input data. The training process of the neural network model will also be described with reference to FIG. 3.

In an example, the ECG signal on which the preprocessing is performed may be input to the neural network model. In another example, the ECG signal in a non-preprocessed state, acquired in 210, may be input to the neural network model. The neural network model extracts the semantic feature to be used for an authentication from the data segment acquired during the preprocessing or the ECG signal.

In 240, the ECG authentication apparatus authenticates a user based on the extracted semantic feature. The ECG authentication apparatus calculates a similarity between the semantic feature and a predefined registered feature or a reference feature corresponding to a target to be compared with the semantic feature. The authentication apparatus determines an authentication result to be a success in authentication or a fail in authentication based on a comparison result of the calculated similarity and a threshold. For example, a cosine similarity between a vector of the semantic feature and a vector of the registered feature is used as a method of measuring the similarity. In this example, according to an increase in the cosine similarity, the similarity between the semantic feature and the registered feature increases. Thus, the ECG authentication apparatus determines that the authentication succeeds when the cosine similarity is greater than or equal to the threshold and determines that the authentication fails when the cosine similarity is less than the threshold. Other methods of calculating the similarity between the semantic feature and the registered feature, other than cosine similarity, are considered to be well within the scope of the present disclosure.

FIG. 3 illustrates an example of training a neural network model based on ECG training data. The operations in FIG. 3 may be performed in the sequence and manner as shown, although the order of some operations may be changed or some of the operations omitted without departing from the spirit and scope of the illustrative examples described. Many of the operations shown in FIG. 3 may be performed in parallel or concurrently. In addition to the description of FIG. 2 below, the above descriptions of FIGS. 1-2, are also applicable to FIG. 3, and are incorporated herein by reference. Thus, the above description may not be repeated here.

Figure 11:
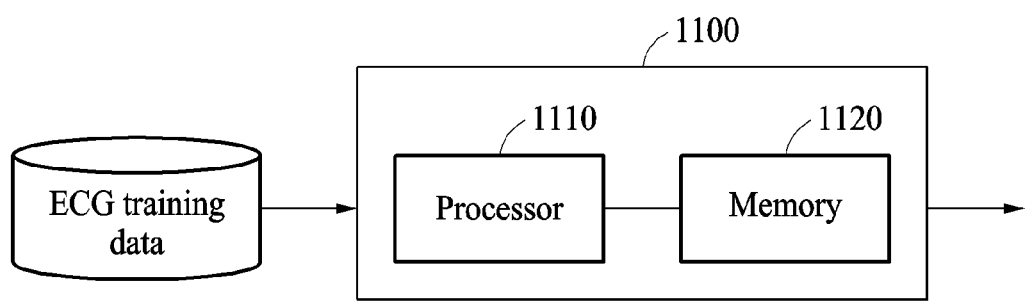
FIG. 11 illustrates an example of a training apparatus.

A training device, for example, a training device 1100 of FIG. 11 trains a neural network model to be used by the ECG authentication apparatus based on ECG training data. Referring to FIG. 3, in 310, the training device receives the ECG training data. In 320, the training device increases the ECG training data. Through filtering, data segmentation based on a fiducial point, and an offset processing, the training device acquires an amount of ECG training data greater than an original amount of ECG training data. Increasing the ECG training data is also referred to as processing data augmentation. When the neural network model is appropriately trained based on various ECG training data, the trained neural network model may extract a feature having an accurate identification skill from the ECG signal.

In an example, operation 320 includes operations 321 through 326. In an example, operations 321 through 326 may be thoroughly or partially performed.

In 321, the training device filters the ECG training data using a filter. The training device removes noise included in the ECG training data through the filtering. For example, the training device filters the ECG training data using a band pass filter having a fixed passband. Also, the training device acquires ECG training data having various frequency bands using a plurality of band pass filters corresponding to different passbands.

In 322, the training device detects at least one fiducial point from the filtered ECG training data. The training device extracts at least one of a peak point of the filtered ECG training data and at least one minimum point close to the peak point, and sets a detected point to be a fiducial point. An ECG signal has a plurality of maximum points and minimum points. Among the maximum points and minimum points, minimum points are formed close to the peak point. The training device detects a fiducial point based on at least one of the peak point and left and right minimum points close to the peak point, the peak point and the left minimum point close to the peak point, or the peak point and the right minimum point close to the peak point from the filtered ECG training data.

In 323, the training device acquires a plurality of data segments having different lengths from the filtered ECG training data based on the at least one fiducial point. For example, the training device acquires data segments having different lengths defined in advance based on the peak point and data segments having difference lengths defined in advance based on a minimum point close to the peak point from the filtered ECG training data.

To increase the ECG training data, the training device performs operation 325 and operation 326, selectively. The training device performs offset and normalization on the data segments in an additional processing of 325 and 326, respectively. The additional processing is also referred to as a disturbance processing. The ECG training data may be diversified through the additional processing.

In 324, the training device selects a fiducial point to perform the offset on a current data segment. In 325, the training device performs the offset on the current segment based on the selected fiducial point. For example, when the peak point is selected as the fiducial point in the data segment, the training device acquires a plurality of data segments having different lengths based on the peak point. In 326, the training device normalizes the data segments to have the same length after the offset.

The training device performs a data augment processing and the disturbance processing on the ECG training data and acquires the augmented ECG training data in various forms. A number of items of the augmented ECG training data corresponds to "a number of filters having different passbands*a number of fiducial points*a number of data segments having difference lengths".

In general, the ECG training data may be insufficiently provided to train the neural network model. In augmenting the ECG training data, meaningful data increases in the original ECG training data. By training the neural network model based on a large amount of ECG training data including the meaningful data, a performance of the neural network model for extracting a distinctive semantic feature from an ECG may be improved.

When ECG training data collected from one user is augmented, a collected time of the ECG training data or a heart rate may include a relatively large difference. Through the data augmentation processing of the ECG training data, the training device increases an amount of meaningful data in the original ECG training data, and improves the performance of the neural network model corresponding to the difference in the heart rate or a collection environment of the ECG training data.

In 330, the training device trains the neural network model to be used for an ECG authentication based on the augmented training data. The neural network model is trained based on a deep training method. The deep training method indicates a machine learning algorithm for attempting a high-level abstraction by combining various non-linear transformation schemes. The neural network model trained based on the deep training method includes an input layer, an output layer, and at least one hidden layer located between the input layer and the output layer.

In one example, the training device trains the neural network model based on an identification signal and a verification signal. In an example, the identification signal indicates a signal used to identify an object corresponding to a first ECG, and the verification signal indicates a signal used to verify whether the object corresponding to the first ECG matches an object corresponding to a second ECG. The identification signal and the verification signal are also referred to as a supervision signal.

The neural network model increases a difference in semantic feature included in the ECG training data of different objects and reduces a similarity in semantic feature between the objects in a feature space.

In an example, operation 330 includes operations 331 and 332.

In 331, the training device trains a plurality of candidate neural network models for each item of the augmented ECG training data. Each of the trained candidate neural network models corresponds to a frequency passband, a type of a fiducial point, the number of fiducial points, and a length of a data segment. Thus, the training device acquires candidate neural network models corresponding to "the number of filters having different passbands*the number of fiducial points*the number of data segments having different lengths".

For example, after the data augmentation processing and the disturbance processing are performed, 261 data segments are acquired, 261=29 (the number of filters having different passbands)*3 (the number of fiducial points)*3 (the number of data segments having different lengths). The training device acquires 261 trained candidate neural network models by training a candidate neural network model for each of the 261 data segments independently of one another.

Each candidate neural network model includes a plurality of layers. A node corresponding to each entity is located in an uppermost layer that is an output layer of the candidate neural network model. For example, a previous layer of a last layer of a neural network model is a fully connection layer, and the last layer is a soft-max including a plurality of nodes. In this example, the plurality of nodes respectively corresponds to the plurality of entities and thus, the number of nodes is the same as the number of entities.

The training device trains the candidate neural network models based on a supervised training method. A supervision signal used for the supervised learning is a signal to be compared with a signal output from the candidate neural network model. Also, the supervision signal is used for adjusting a weight of neurons included in the candidate neural network models. The supervision signal includes an identification signal and a verification signal. The identification signal is used for determining whether a result of identification performed on an entity of a type corresponding to the ECG training data through a nonlinear mapping of layers is valid. The verification signal is used for determining whether a result obtained by verifying whether two items of ECG training data belong to the same entity through the nonlinear mapping of the layers is valid.

The training device compares a signal output from the uppermost layer of the candidate neural network model to the supervision signal. The training device adjusts the weight of the neurons included in the candidate neural network model such that a value of an error function indicating a comparison result is less than or equal to a threshold. In this example, the error function may be a function used to measure a difference between the supervision signal and the signal output from the candidate neural network model. The training device uses, for example, a cross-entropy loss function as the error function.

The training device adjusts the weight of the neurons included in the candidate neural network model by minimizing a cross-entropy according to Equation 1. Equation 1 represents a loss function corresponding to the identification signal. The training device adjusts the weight of the neurons to reduce the output value in Equation 1. Through this, the training device increases a difference between semantic features in ECG training data of different entities in a feature space and a similarity between the semantic features.

$$L_{ident}(f, t, \theta_{id}) = -\sum_{i=1}^{n} p_i \log \hat{p}_i = -\log \hat{p}_t \quad \text{[Equation 1]}$$

In Equation 1, f denotes an output of a last fully connected layer of the candidate neural network model and the output indicates a semantic feature extracted from the ECG training data, t denotes an index of an actual type of entity, $\theta_d$ denotes a parameter of the soft-max layer corresponding to the last layer of the candidate neural network model, $p_i$ denotes an actual probability distribution corresponding to the ECG training data. Here, if i=t, $p_i$=1. If not i=t, $p_i$=0. $\hat{p}_i$ denotes a probability distribution estimated using the candidate neural network model. In Equation 1, a performance of the candidate neural network model increases according to an increase in a prediction probability of an actual type entity t and a decrease in a value of the loss function of Equation 1.

Equation 2 represents a loss function corresponding to the verification signal. The training device extracts a feature from the same entity and performs a training process for verification. A pair of items of ECG training data extracted from the same entity is referred to as a positive sample, for example, y being equal to +1. A pair of items of ECG training data is referred to as a negative sample, for example, y being equal to zero.

$$L_{verif}(x_i, y_i, x_j, y_j) = \quad \text{[Equation 2]}$$
$$\begin{cases} 0.5\|f(x_i) - f(x_j)\|^2 & y_{ij} = 1 \\ 0.5\max(0, m - \|f(x_i) - f(x_j)\|)^2 & y_{ij} = 0 \end{cases}$$

In Equation 2, $x_i$ and $x_j$ each denote the ECG training data, $f_i$ and $f_j$ each denote a semantic feature corresponding to the ECG training data. If $y_{ij}$=1, a Euclidean distance between the semantic features of $x_i$ and $x_j$ minimized and thus, $x_i$ and $x_j$ belong to the same entity. If $y_{ij}$=0, the distance between the semantic features of $x_i$ and $x_j$ is greater than m although the Euclidean distance is minimized. Thus, $x_i$ and $x_j$ belong to different entities, respectively. Here, m is a predetermined constant.

The training device selects the pair of items of ECG training data until a parameter converges to a predetermined value. When a relatively great amount of ECG training data is provided, a probability that the selected pair of items of ECG training data is the positive sample is relatively low. To increase the probability that the selected items of ECG training data is the positive sample, the training device divides the ECG training data into a plurality of groups, for example, mini-batches, and searches each of the groups for a pair of positive samples. By searching each of the groups for the pair of positive samples, the training device generates a greater number of pairs of positive samples in comparison to a case in which one pair of positive samples is selected at one time. A loss function of each of the groups is obtained by correcting Equation 1 and Equation 2. The obtained loss function is represented by Equation 3 as below.

$$\text{Loss} = -\sum_{l=1}^{N}\sum_{i=1}^{n} p_i \log \hat{p}_i + \frac{1}{2} \cdot \lambda \cdot \sum_{l,k=1}^{N} \|f_l - f_k\|_2^2 \cdot y_{lk} \quad \text{[Equation 3]}$$
$$= -\sum_{l=1}^{N}\sum_{i=1}^{n} p_i \log \hat{p}_i + \lambda \cdot Tr(F^T F L)$$

In Equation 3, N denotes a total number of samples included in a small group, $di=\Sigma_{j=1}^{N}$, $F=[f_1, f_2, \ldots, f_N]$, and L=D−Y. $\lambda$ denotes a weight between two items and Tr( ) denotes a trace calculation. In the loss function Loss, a portion associated with an $i^{th}$ sample is represented by Equation 4.

$$l_i = -\sum_{i=1}^{n} p_i \log \hat{p}_i + 2\lambda(2f_i^T F L_i - f_i^T f_i L_{ii}) \quad \text{[Equation 4]}$$

$$p_i = \frac{e^{\theta_i \cdot f}}{\sum_{j=1}^{n} e^{\theta_j \cdot f}}$$

The training device calculates a gradient of $x_i$ using Equation 4. After calculating the gradient, the training device enters an optimizing process. In one example, the training device updates each parameter of the candidate neural network model based on a back propagation method.

The back propagation method includes a forward propagation and an error back propagation. A node of an input layer receives information input from an outside, and transfers the received information to an intermediate layer. The intermediate layer is a data processing layer in the candidate neural network model and performs a data exchange. The intermediate layer includes at least one hidden layer. After information to be transferred to each node of an output layer is processed by a last hidden layer, the forward propagation is performed. Thereafter, the training device outputs a data processing result through the output layer.

When an actual output of the candidate neural network model differs from an expected output, the training device performs the error back propagation to adjust a parameter, for example, the weight of neurons, of the candidate neural network model. The training device corrects a weight of each layer included in the candidate neural network model using an error gradient descent method based on a difference between the actual output and the expected output of the candidate neural network model. As such, the training device corrects weights, starting from the output layer, the hidden layer, and the input layer. The training device adjusts the weight of each layer by repetitively performing the forward propagation and the error back propagation and completes the training process. The foregoing training process is repetitively performed by a preset number of training times or until the difference between the actual output and the expected output of the candidate neural network model is less than the threshold.

In 332, the training device selects at least one candidate neural network model from the candidate neural network models based on accuracies of candidate semantic features extracted by the candidate neural network models. The training device determines a final neural network model to be used for ECG signal authentication based on the selected at least one candidate neural network model.

For example, the training device selects a candidate neural network model that outputs a candidate semantic feature having a highest accuracy from the candidate neural network models. Also, the training device selects at least one candidate semantic feature determined as having a relatively high accuracy from a plurality of candidate semantic features using a greedy algorithm. A candidate neural network model corresponding to the selected semantic feature is determined to be the final network model. For example, the training device uses a forward greedy algorithm and a backward greedy algorithm to select the candidate semantic feature having a high accuracy from the plurality of candidate semantic features. The training device calculates an accuracy of each of the candidate semantic features using the forward greedy algorithm and selects a candidate semantic feature having the highest accuracy from the candidate semantic features. From the remaining candidate semantic features, the training device selects a candidate semantic feature that maximizes the accuracy when combined with the selected semantic feature. The foregoing process is repetitively performed until the number of selected semantic features reaches a first number of semantic features set in advance or the accuracy does not increase.

Using the backward greedy algorithm, the training device removes one candidate semantic feature that maximizes the accuracy when combined with the unselected remaining candidate semantic features from the candidate semantic features selected using the forward greedy algorithm. The foregoing process is repetitively performed until the number of unselected or non-removed semantic features reaches a second number of semantic features set in advance or the accuracy does not increase. In an example, the second number of semantic features is less than or equal to the first number of semantic features.

FIGS. 4A through 4E illustrate examples of a filtering result of ECG training data.

A training device filters ECG training data using a filter. For example, the training device filters the ECG training data using a band pass filter having different frequency passbands. Filtering results obtained in such process are shown in FIGS. 4A through 4E. The training device removes noise from the ECG training data through a filtering process. Using a band pass filter having a plurality of different passbands, the training device acquires a greater amount of ECG training data including meaningful information when compared to a case in which a filter having a single fixed passband is used. A plurality of passbands of the band pass filter used in the filtering process is shown in Table 1 as below.

TABLE 1

| 1-10 Hz | 1-15 Hz | 1-20 Hz | 1-30 Hz | 1-40 Hz |
| 1-50 Hz | 3-15 Hz | 3-20 Hz | 3-30 Hz | 3-40 Hz |
| 3-50 Hz | 5-15 Hz | 5-20 Hz | 5-30 Hz | 5-40 Hz |
| 5-50 Hz | 10-20 Hz | 10-30 Hz | 10-40 Hz | 10-50 Hz |
| 15-25 Hz | 15-35 Hz | 15-45 Hz | 20-30 Hz | 20-40 Hz |
| 20-50 Hz | 25-35 Hz | 25-45 Hz | 35-45 Hz | |

As shown in Table 1, a start frequency of a passband of the band pass filter is in a range between 1 hertz (Hz) and 35 Hz, and an end frequency is in a range between 10 Hz and 50 Hz. The passbands in Table 1 may each be a frequency segment or a frequency passband allowing the ECG training data to incorporate a great amount of meaningful information and reducing the noise.

As illustrated in FIGS. 4A through 4E, when the different passbands are used, different filtering results are obtained. According to an increase in a bandwidth of the passband, an amount of noise included in the filtered ECG training data also increases. For example, an amount of noise included in a filtering result decreases in an order of a passband of 1 to 40 Hz, a passband of 1 to 30 Hz, a passband of 3 to 30 Hz, and a passband of 3 to 15 Hz and thus, a smoothness of a graph of the ECG training data increases in the order. Also, the wider the bandwidth of the passband, the greater an amount of salient information on the ECG signal is acquired through the filtering. By using the band pass filters having different passbands, respectively, the training device acquires ECG training data including a greater amount of salient information when compared to a case in which a band pass filter having a single passband is used.

Figure 5:
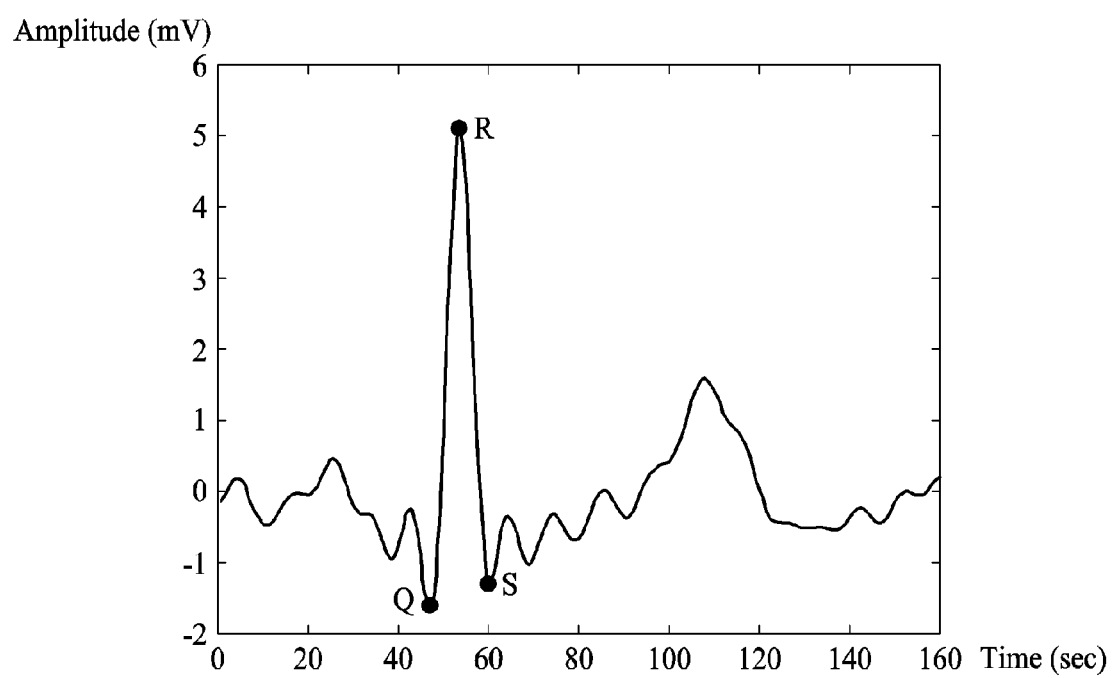
FIG. 5 illustrates an example of a fiducial point detected from ECG training data.

FIG. 5 illustrates an example of a fiducial point detected from ECG training data.

Referring to FIG. 5, ECG training data has a plurality of maximum points or minimum points, and a point Q and a point S are formed as minimum points closest to a point R corresponding to a peak point.

A training device sets one of the point R, the point Q, and the point S to be a fiducial point. In an example, the training device sets the point R to be the fiducial point. Based on the point R, the training device acquires data segments having different lengths of, for example, 160 sample points, 190 sample points, or 220 sample points. The data segments acquired based on the point R includes overall information associated with a single heartbeat. For example, one data segment having the length of 160 sample points corresponds to a length of "63 samples points before the point R+the point R+96 sample points after the point R".

In an example, the training device sets the point Q or the point S to be the fiducial point and acquires data segments having a relatively small length corresponding to 30 through 50 sample points. The data segments acquired based on the point Q or the point S includes partial information associated with the heartbeat.

FIGS. 6A through 6I illustrate examples of data segments acquired based on a fiducial point.

Figure 6A:
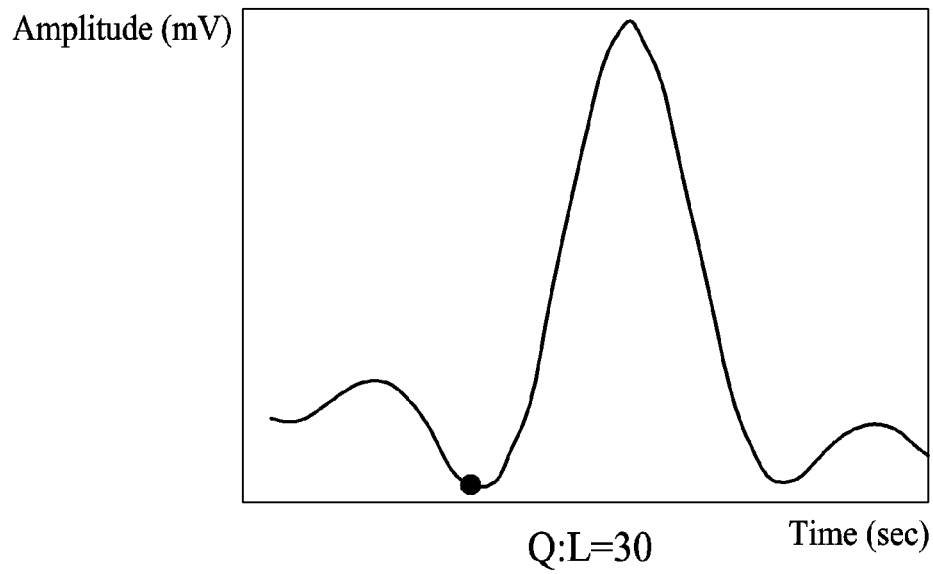
FIGS. 6A through 6I illustrate examples of data segments acquired based on a fiducial point.
Figure 6B:
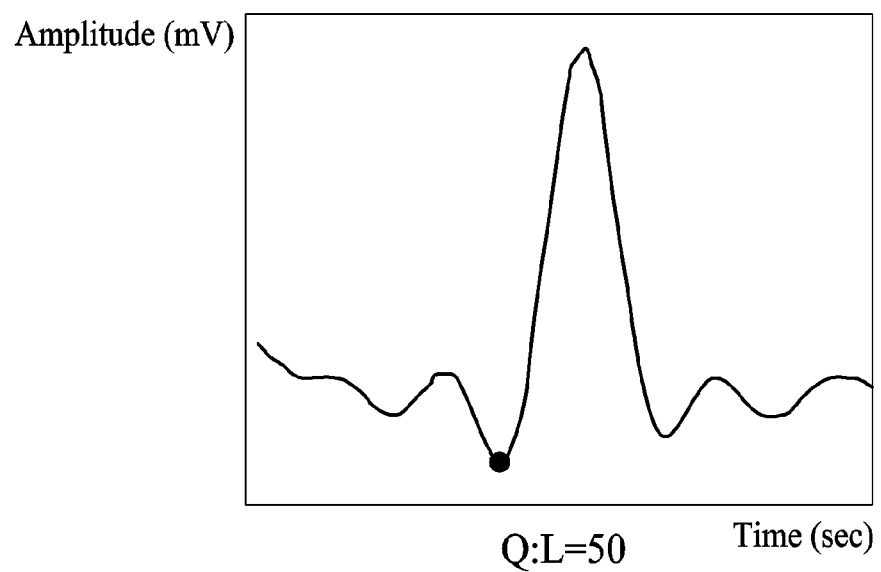
Figure 6C:
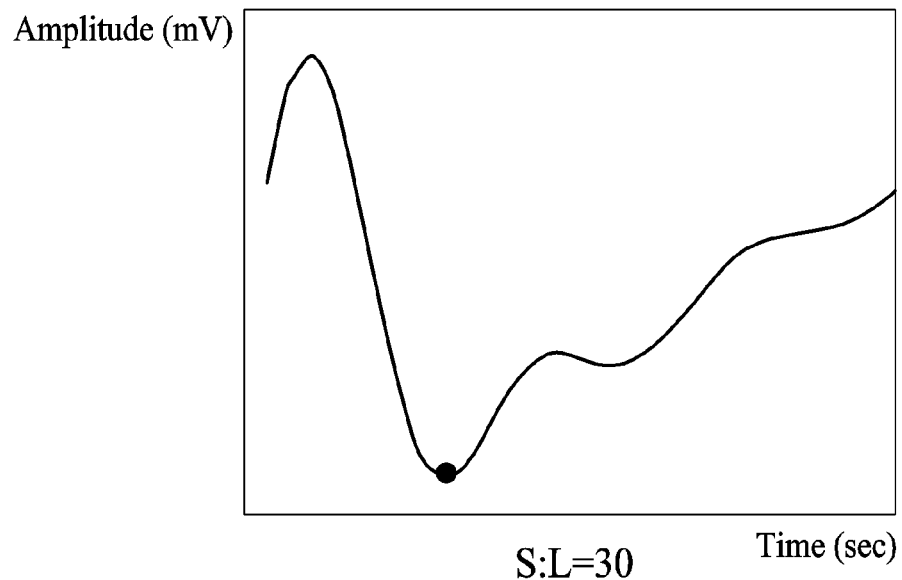
Figure 6D:
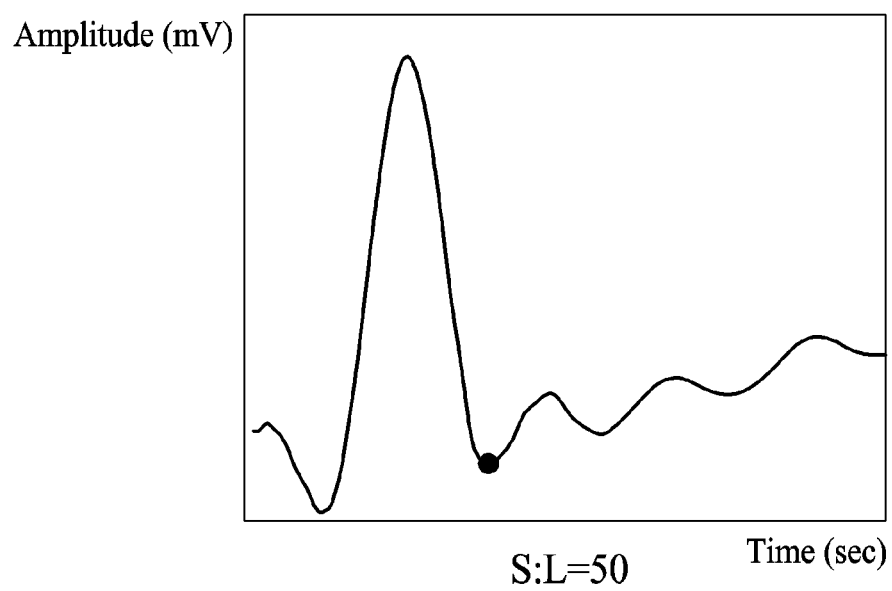
Figure 6E:
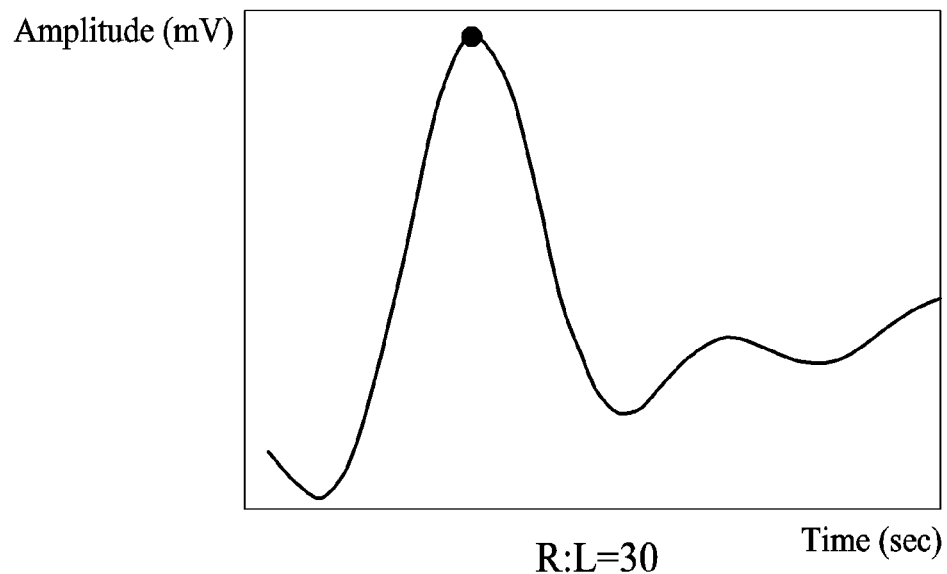
Figure 6F:
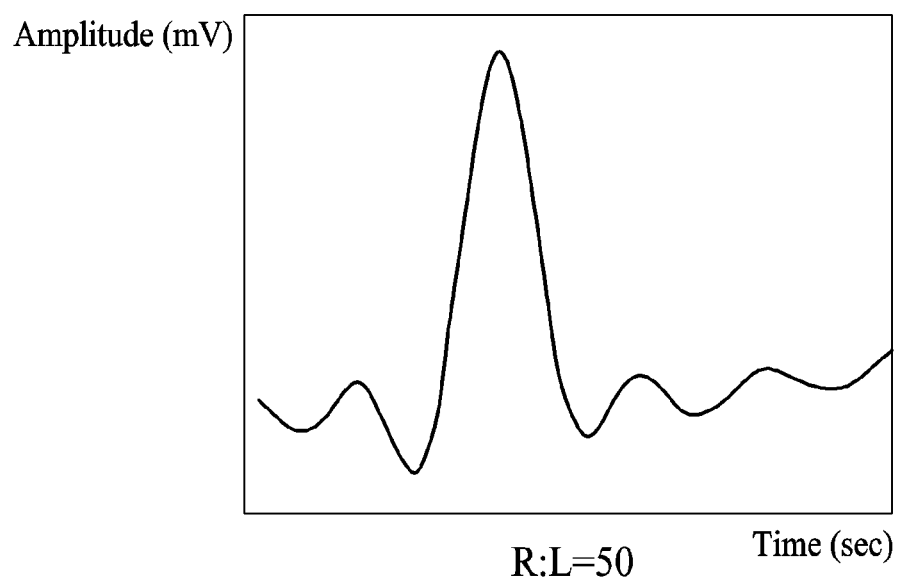
Figure 6G:
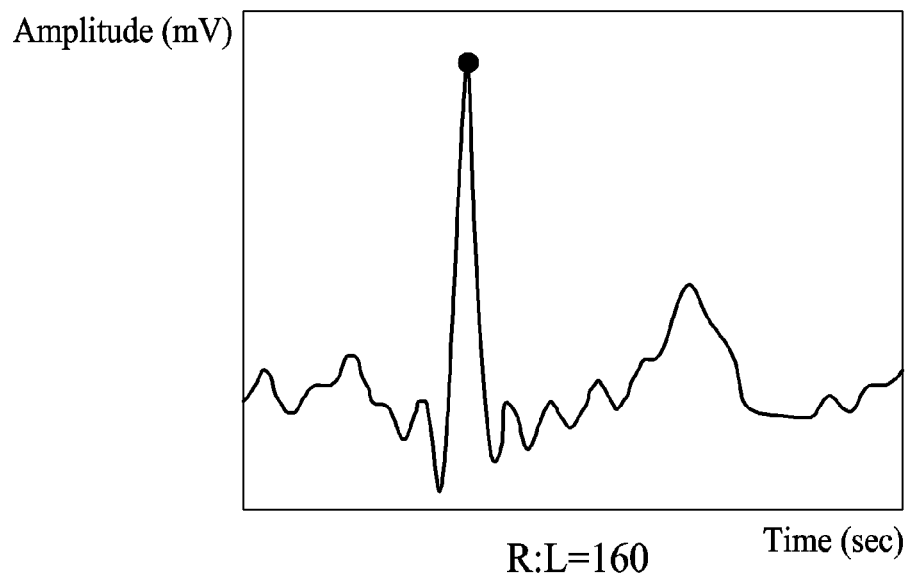
Figure 6H:
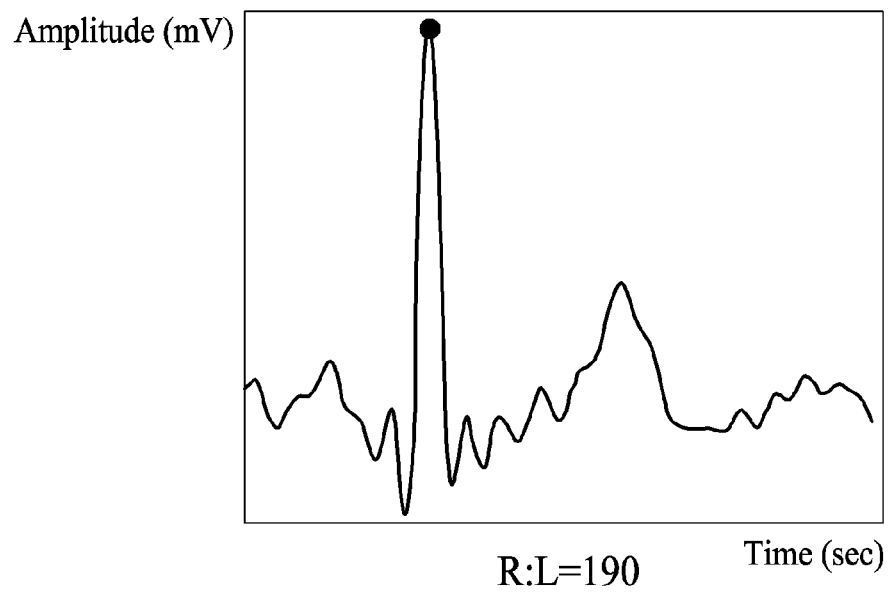
Figure 6I:
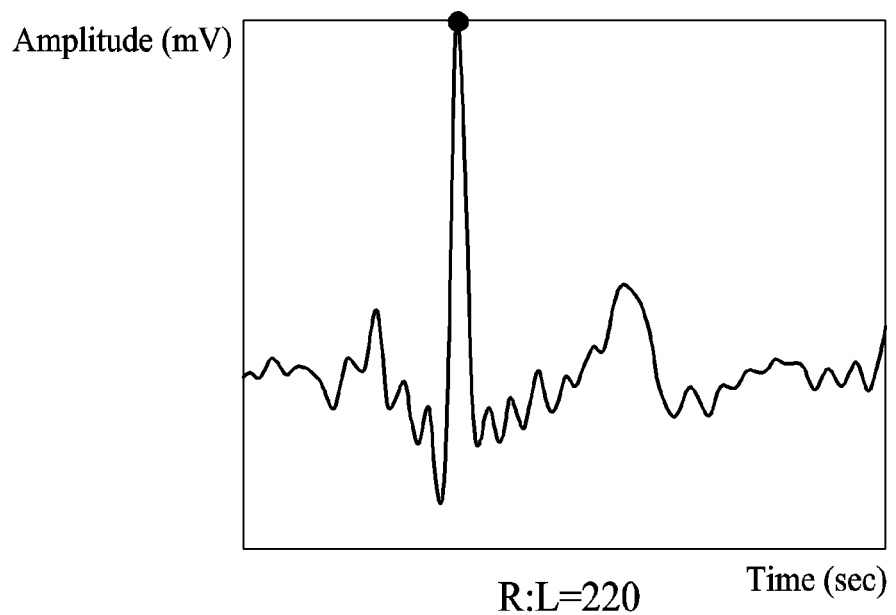

FIGS. 6A through 6I illustrates data segments having different lengths based on a fiducial point selected from a point R, a point Q, a point S. Referring to FIG. 6A, a graph "Q:L=30" represents a data segment having a length of 30 sample points based on the point Q. As illustrated in FIGS. 6A through 6I, data segments acquired based on the point Q and the point S have lengths less than a length of a data segment acquired based on the point R. A graph of the data segment acquired based on the point Q or the point S selected as the fiducial point represents a portion of heart beats. In contrast, a graph of the data segment acquired based on the point R selected as the fiducial point represents full information associated with the heart beats.

Table 2 shows a plurality of data segments acquired based on types of the point R, the point Q, and the point S.

TABLE 2

|  | Before R | After R | Total length |
| --- | --- | --- | --- |
| R-160 | 63 | 96 | 160 |
| R-190 | 63 | 126 | 190 |
| R-220 | 73 | 146 | 220 |
| R-30 | 9 | 20 | 30 |
| R-50 | 19 | 31 | 50 |

|  | Before Q | After Q | Total length |
| --- | --- | --- | --- |
| Q-30 | 9 | 20 | 30 |
| Q-50 | 19 | 30 | 50 |

|  | Before S | After S | Total length |
| --- | --- | --- | --- |
| S-30 | 9 | 20 | 30 |
| S-50 | 19 | 30 | 50 |

FIGS. 7A through 7D illustrate examples of a result obtained by performing additional data processing on ECG training data.

A training device selectively performs a data augmentation processing for each data segment. The training device also uses a length of a data segment and a fiducial point used as a reference for acquiring the data segment in the additional data processing. The training device performs an offset on both ends of the data segment while maintaining a baseline of ECG training data. After the offset, the training device normalizes the data segment to have the same length.

For example, when a point R is set as a fiducial point, and when a data segment set to have 63 sample points before the point R and 96 sample points after the point R is present, a total length of the data segment may be 160 sample points. As shown in Table 3, the training device acquires data segments having different lengths through an additional data processing including a first case and a second case. In Table 3, numbers indicate the number of sample points.

TABLE 3

|  | Before point R | After point R | Total length |
| --- | --- | --- | --- |
| Reference case | 63 | 96 | 160 |
| First case | 61 | 93 | 155 |
| Second case | 65 | 99 | 165 |

Figure 7A:
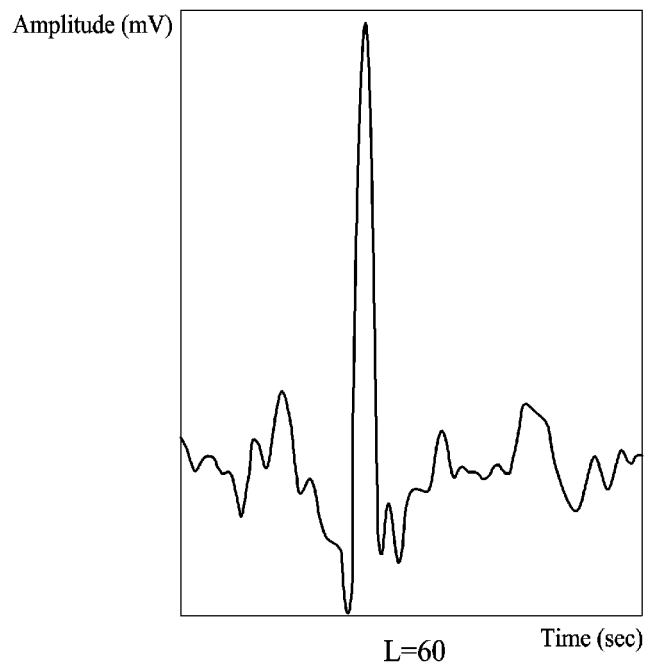
FIGS. 7A through 7D illustrate examples of a result obtained by performing additional data processing on ECG training data.
Figure 7B:
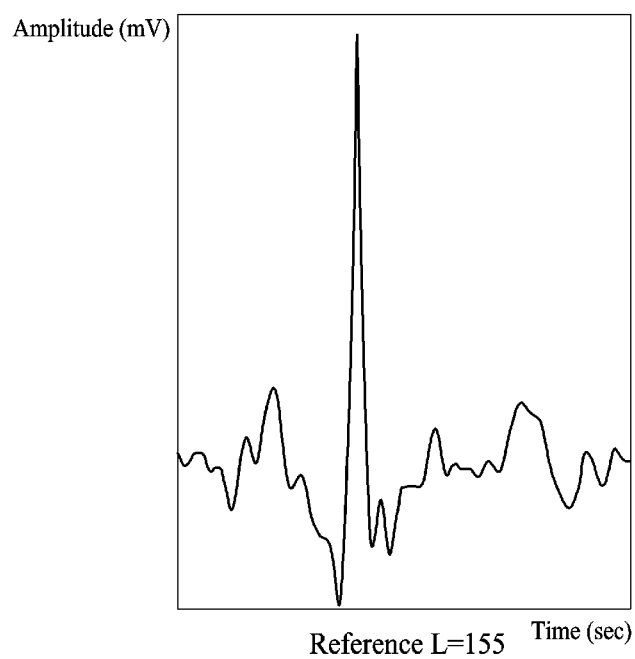
Figure 7C:
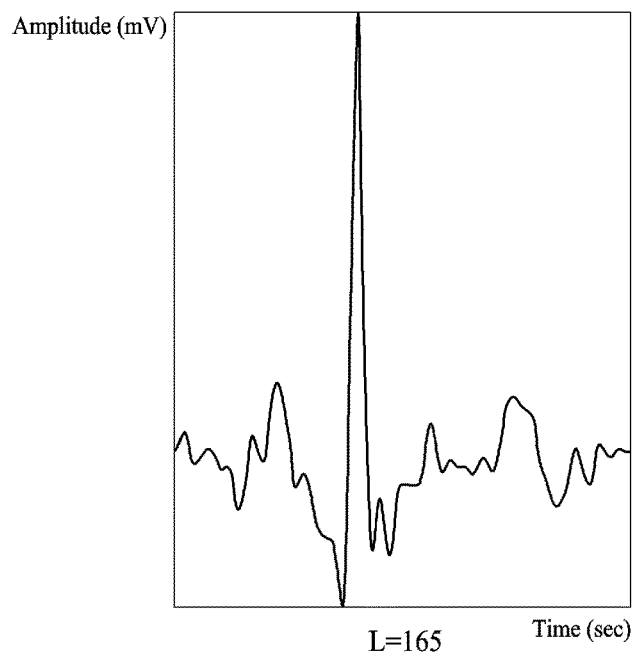

FIGS. 7A through 7C illustrate data segments having a length of 160 sample points, a length of 155 sample points, and 165 sample points based on a point R as a fiducial point. The data segments have different lengths with respect to the same ECG training data. A training device performs an offset on a data segment of a reference case to generate data segments having different lengths as shown in a first case and a second case.

Figure 7D:
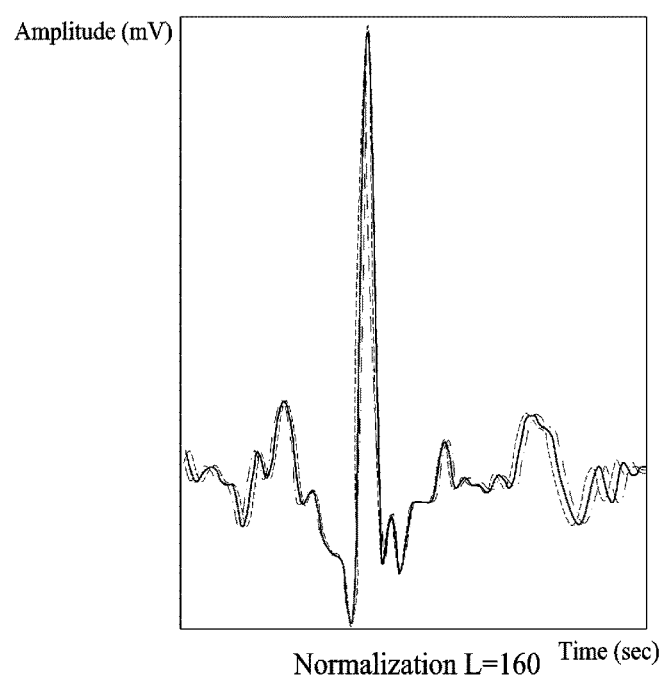

Referring to FIG. 7D, the training device normalizes the data segments of FIGS. 7A through 7C such that the data segments have the same length. The training device adjusts the lengths of the data segments of the first case and the second case such that the data segments each have 63 sample points before the point R similarly to the reference case.

For example, in the graphs of FIGS. 7B and 7C, the training device normalizes 61 sample points and 65 sample points to be 63 sample points. Also, the training device performs normalization such that the number of sample points after the point R corresponds to 96 sample points. For example, in the graphs of FIGS. 7B and 7C, the training device adjusts 93 sample points and 99 sample points to be 96 sample points. As shown in a graph of FIG. 7D, the training device maintains each of the data segments of FIGS. 7A through 7C to have the length of 160 sample points. The training device similarly performs the normalization on data segments corresponding to different lengths or different fiducial points through the foregoing process and acquires various items of ECG training data. In FIGS. 7A through 7D, L denotes a length of a data segment and the length corresponds to the number of sample points configuring the data segment.

Figure 8A:
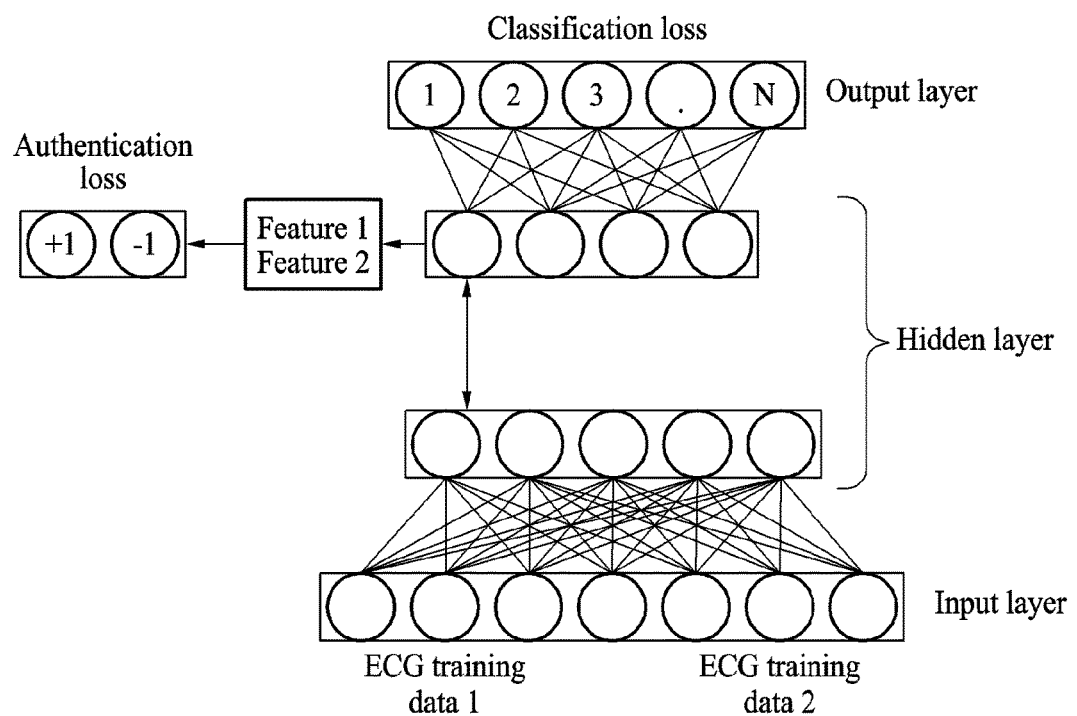
FIG. 8A illustrates an example of a neural network model.
Figure 8B:
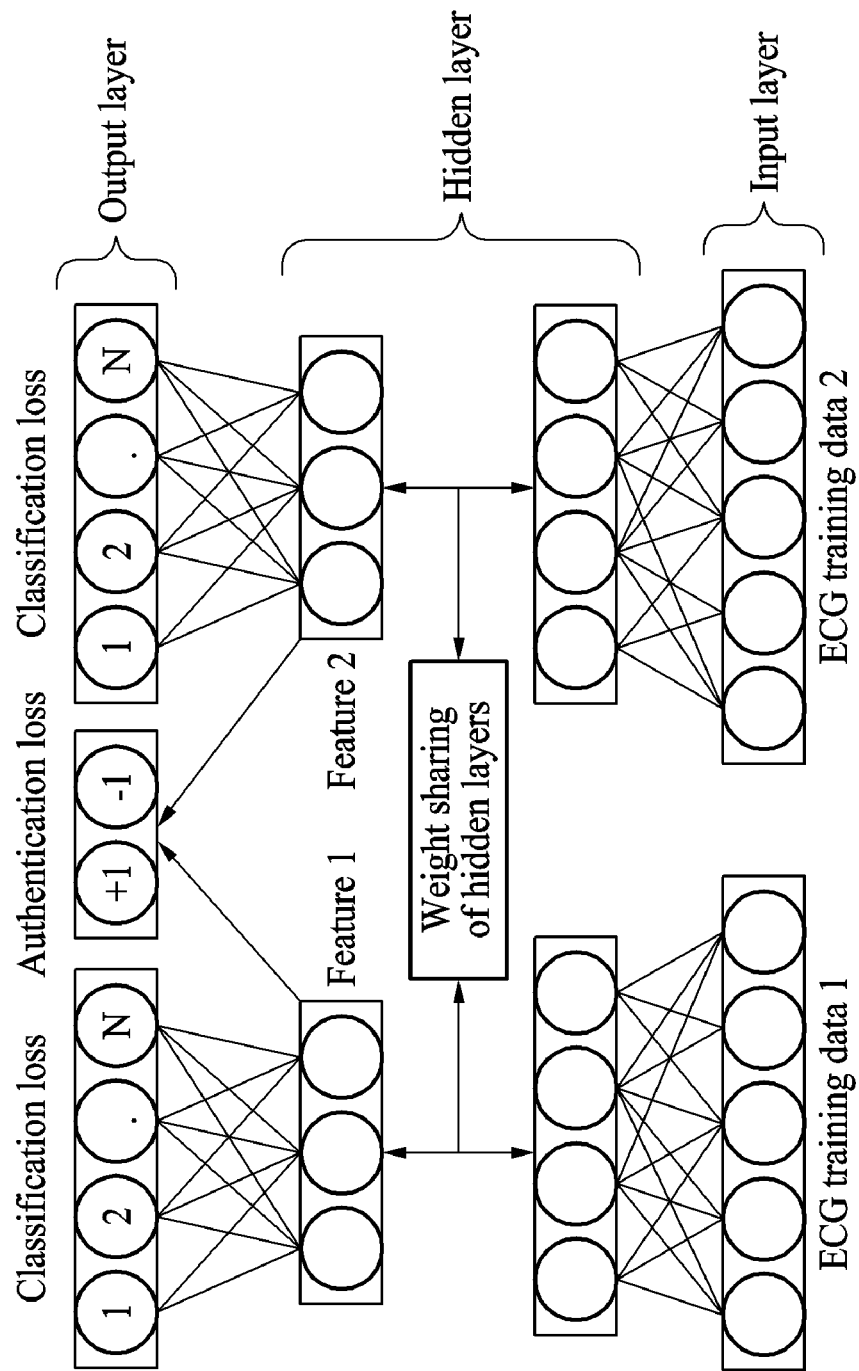
FIG. 8B illustrates an example of a neural network model.

FIG. 8A illustrates an example of a neural network model, and FIG. 8B illustrates another example of a neural network model.

In an example of a neural network model of FIG. 8A, a pair of items of ECG training data is input to an input layer of a candidate neural network model. A lowermost layer may be the input layer and a number of nodes or neurons included in the input layer may be the same as a size of a dimension of ECG training data. An uppermost layer may be an output layer. The output layer is trained based on an identification signal. A hidden layer is located between the input layer and the output layer. An output of a last hidden layer indicates a learned semantic feature. A pair of features output from the last hidden layer corresponds to one authentication output, for example, +1 or −1.

In an example of a neural network model of FIG. 8B, a pair of items of ECG training data are input to two neural network models. A weight of a hidden layer is shared between the two neural network models. In the two neural network models, an output of a previous hidden layer of the last hidden layer is determined to be a semantic feature.

Figure 9:
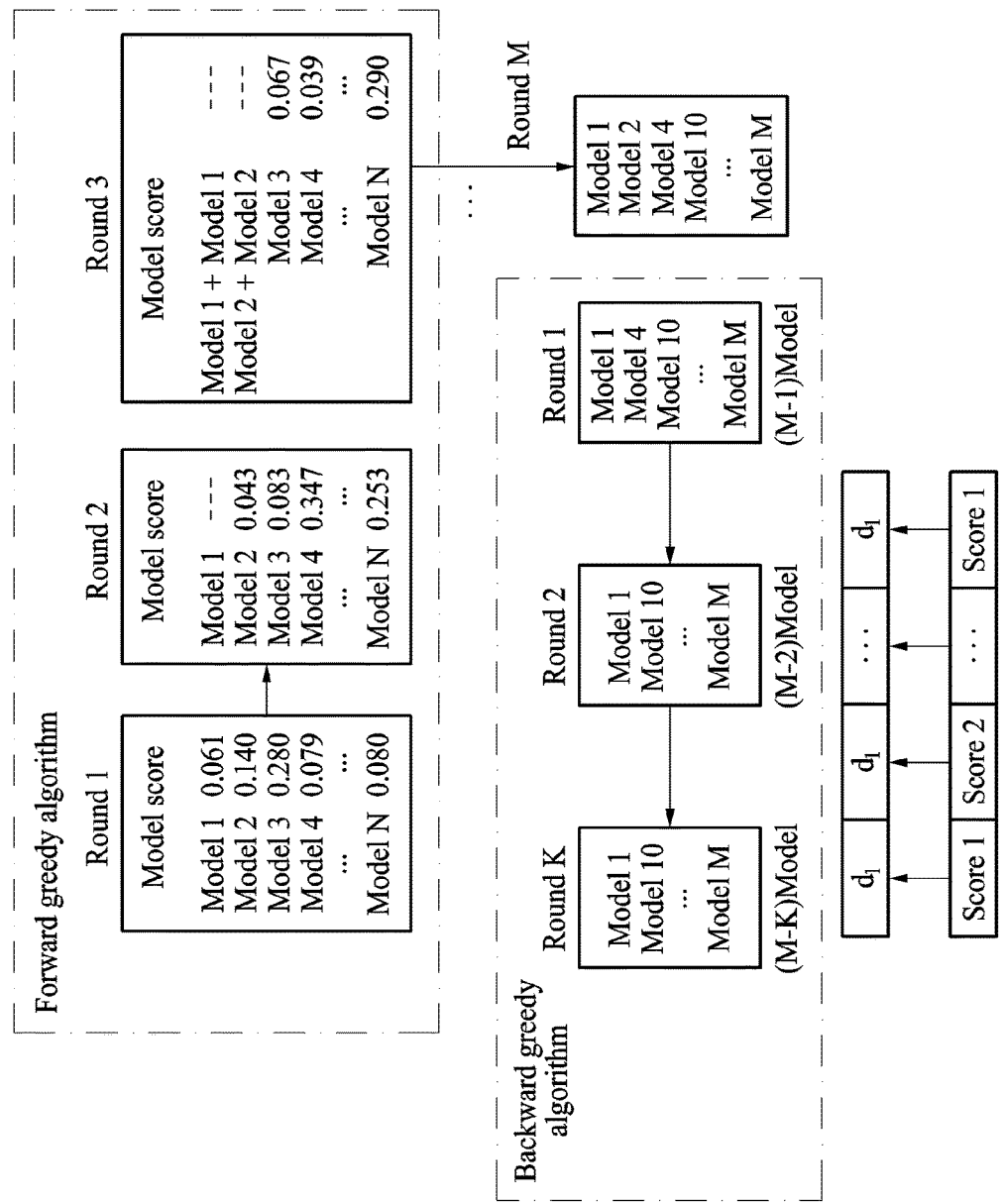
FIG. 9 illustrates an example of selecting an optimal candidate neural network model from candidate neural network models using a greedy algorithm.

FIG. 9 illustrates an example of selecting an optimal candidate neural network model from candidate neural network models using a greedy algorithm.

A training device acquires a plurality of candidate neural network models as a training result. Not all of the candidate neural network models may provide a high performance. The training device selects a candidate neural network model providing a highest performance.

The training device extracts a candidate semantic feature from ECG training data using each of the candidate neural network models. For example, the training device selects at least one candidate semantic feature satisfying a reference from a plurality of candidate semantic features using a greedy algorithm. The training device uses a forward greedy algorithm and a backward greedy algorithm to select a candidate semantic feature.

In the forward greedy algorithm, the training device evaluates a performance of a single candidate neural network model and select a candidate neural network model corresponding to the highest performance. An evaluation of the candidate neural network model may be performed based on a candidate semantic feature corresponding to the candidate neural network model. In an example of FIG. 9, according to a decrease in a value of a model score, a performance of a candidate neural network model increases. Based on the forward greedy algorithm, the training device selects a candidate neural network model 1 at round 1. Hereinafter, the candidate neural network model is also referred to as a model. At round 2, the training device selects, as a model 2, a model that obtains the highest performance when combined with the model 1 corresponding to the model selected in a previous round, round 1 from remaining models, for examples, the model 2 through a model N. Such selecting process may be repetitively performed until the number of selected candidate semantic features reaches a first number of features set in advance or until an accuracy of the candidate semantic feature does not increase.

The backward greedy algorithm is used to complement the forward greedy algorithm. It is difficult to correct an error occurring at an earlier round using the forward greedy algorithm. For example, since the model 1 is selected at the round 1, the model 1 is not removed from finally selected candidate neural network models although a combination of the model 2 selected at the round 2 and a model 4 selected at round 3 provides the highest performance. In other words, when the model 1 is selected at the round 1, the combination of the model 2 and the model 4 may not be selected although the combination provides the highest performance.

The training device evaluates performances of M models at every round using the backward greedy algorithm. Through such evaluation, the training device removes one model and evaluates performances of combinations of remaining models. The evaluation of the model may be performed based on a candidate semantic feature output from the model. In this example, a model that maximizes a performance when the model is removed may be selected as a model to be removed. The foregoing process may be repetitively performed until the number of unselected or non-removed remaining candidate semantic features reaches a second number of features set in advance or until an accuracy of the candidate semantic feature does not increase. In an example, the second number of features may be less than or equal to the first number of features.

Figure 10:
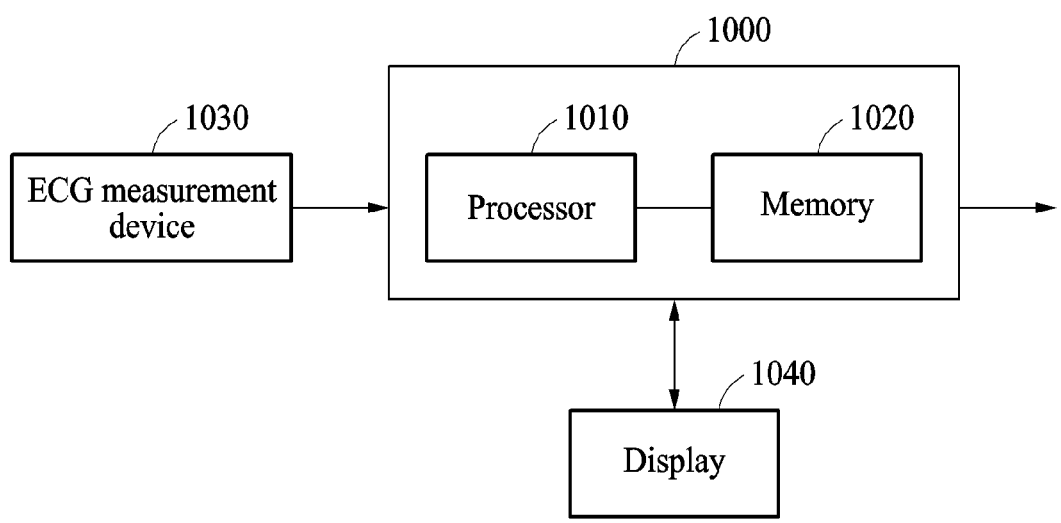
FIG. 10 illustrates an example of an ECG authentication apparatus.

FIG. 10 illustrates an example of an ECG authentication apparatus.

Referring to FIG. 10, an ECG authentication apparatus 1000 includes a processor 1010, a memory 1020, and a display 1040.

The processor 1010 performs at least one of operations described with reference to FIGS. 1 and 2. For example, the processor 1010 performs ECG authentication based on an ECG signal of a user acquired through an ECG measurement device 1030. Depending on an example, the ECG measurement device 1030 may be included in the ECG authentication apparatus 1000. The processor 1010 extracts a semantic feature from the ECG signal using a neural network model and performs the ECG authentication by comparing the extracted semantic feature and a registered feature registered in advance.

The memory 1020 stores instructions for performing at least one of the operations described with reference to FIGS. 1 and 2, or stores results and data acquired through an operation of the ECG authentication apparatus 1000. In some examples, the memory 1020 includes a non-temporary computer-readable medium as described below.

When an ECG authentication process is completed, the ECG authentication apparatus 1000 provides an ECG authentication result to a user using, for example, a display 1040, a speaker, or a vibration feedback sensor. In an example, the display 1040 may be a physical structure that includes one or more hardware components that provide the ability to render a user interface and/or receive user input. The display 1040 can encompass any combination of display region, gesture capture region, a touch sensitive display, and/or a configurable area. In an example, the display 1040 is an external peripheral device that may be attached to and detached from the ECG authentication apparatus 1000. The display 1040 may be a single-screen or a multi-screen display. A single physical screen can include multiple displays that are managed as separate logical displays permitting different content to be displayed on separate displays although part of the same physical screen. The display 1040 may also be implemented as an eye glass display (EGD), which includes one-eyed glass or two-eyed glasses.

In an example, the ECG authentication apparatus 1000 generates a control signal allowing an access of the user in response to a success in authentication. In an example, the ECG authentication apparatus 1000 restricts the access of the user in response to a fail in authentication.

FIG. 11 illustrates an example of a training apparatus. Referring to FIG. 11, a training apparatus 1100 includes a processor 1110, a memory 1120.

The processor 1110 performs at least one of operations described with reference to FIGS. 3 through 9. For example, the processor 1110 trains a neural network model based on ECG training data. The processor 1110 performs signal processing for increasing the ECG training data and trains each candidate neural network models based on the ECG training data. The processor 1110 selects at least one candidate neural network models to be used for ECG authentication from candidate neural network models based on an accuracy of candidate semantic features output by the candidate neural network models. The memory 1120 stores instructions for performing at least one of the operations described with reference to FIGS. 3 through 9, or stores data and results acquired through an operation of the training apparatus 1100.

The apparatuses, units, modules, devices, and other components described herein are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2-3 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), electrically erasable programmable read-only memory (EEPROM), random-access memory (RAM), dynamic random access memory (DRAM), static random access memory (SDRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An electrocardiogram (ECG) authentication method comprising:
    acquiring an ECG signal of a subject;
    filtering the ECG signal using a band pass filter;
    detecting a fiducial point from the ECG signal after filtering;
    acquiring a data segment from the filtered ECG signal based on the fiducial point;
    extracting a semantic feature of the acquired ECG signal using a neural network model; and
    authenticating the subject based on the extracted semantic feature, wherein the neural network model is trained using a candidate neural network model selected from candidate neural network models whose cross-entropy of its uppermost layer has been minimized.

2. The ECG authentication method of claim 1, wherein the extracting of the semantic feature of the ECG signal comprises extracting a semantic feature from the data segment using the neural network model.

3. The ECG authentication method of claim 1, wherein the fiducial point comprises a peak point of the filtered ECG signal and a minimum point close to the peak point.

4. The ECG authentication method of claim 1, wherein the authenticating comprises:
    calculating a similarity between the extracted semantic feature and a registered feature; and
    determining an authentication of the ECG signal based on a comparison of the similarity and a threshold.

5. The ECG authentication method of claim 1, wherein the neural network model is a semantic feature extraction model trained using a deep learning scheme based on ECG training data.

6. The ECG authentication method of claim 1, wherein the fiducial point comprises at least one of: the peak point of the filtered ECG signal, a left minimum point, a right minimum point close to the peak point, the peak point and the left minimum point, or the peak point and the right minimum point.

7. A non-transitory computer-readable storage medium storing instructions that, when executed by a processor, causes the processor to perform the method of claim 1.

8. An electrocardiogram (ECG) authentication apparatus comprising:
a processor configured to:
receive an ECG signal of a subject;
filter the ECG signal using a band pass filter;
extract a semantic feature of the filtered ECG signal using a neural network model; and
authenticate the subject based on the extracted semantic feature, wherein the neural network model is trained by detecting a fiducial point from the ECG signal after filtering and using a candidate neural network model selected from candidate neural network models whose cross-entropy of its uppermost layer has been minimized; and
acquiring a data segment from the filtered ECG signal based on the fiducial point.

9. The training method of claim 8, wherein the training of the neural network model comprises training the neural network model based on an identification signal for identifying an entity corresponding to the ECG training data and an authentication signal for verifying whether items of ECG training data corresponds to the same entity.

10. The ECG authentication device of claim 1, wherein the processor is further configured to receive the ECG signal, measured by another device, using an antenna.

11. A training method comprising:
receiving electrocardiogram (ECG) training data;
augmenting the ECG data; and
filtering the ECG signal using a band pass filter;
training a neural network model for ECG authentication based on the augmented ECG training data;
training candidate neural network models for the augmented ECG training data;
selecting a candidate neural network model from the candidate neural network models by minimizing a cross-entropy based on an uppermost layer of the candidate neural network model, wherein the augmenting comprises detecting a fiducial point from the ECG data after filtering and acquiring a data segment from the filtered ECG signal based on the fiducial point.

12. The training method of claim 11, wherein the filtering of the ECG training data comprises filtering the ECG training data using a band pass filter having different passbands.

13. The training method of claim 11, wherein the filtering of the ECG training data comprises filtering the ECG training data using a band pass filter having a fixed passband.

14. The training method of claim 11, wherein the fiducial point comprises a peak point of the filtered ECG training data and a minimum point close to the peak point.

15. The training method of claim 11, wherein the augmenting of the ECG training data further comprises:
normalizing a data segment obtained through the offset.

16. The training method of claim 11, wherein the training of the neural network model comprises:
training candidate neural network models for each item of the augmented ECG training data; and
selecting a candidate neural network model from the candidate neural network models based on an accuracy of a candidate semantic feature extracted using each of the candidate neural network models.

17. The training method of claim 16, wherein a final neural network model used for the ECG authentication is determined based on the selected candidate neural network model.

18. The training method of claim 16, further comprising:
selecting a second candidate neural network model from the remaining candidate neural network models to increase the accuracy based on the semantic feature corresponding to the second candidate neural network model being combined with the selected candidate semantic feature.

19. The training method of claim 11, wherein the training of the neural network model comprises minimizing a value of a loss function $$L_{ident}(f, t, \theta_{id}) = -\sum_{i=1}^{n} p_i \log \hat{p}_i = -\log \hat{p}_t$$

wherein f denotes an output of a last fully connected layer of the candidate neural network model and the output indicates a semantic feature extracted from the ECG training data, t denotes an index of an actual type of entity, $\theta_{id}$ denotes a parameter of the soft-max layer corresponding to a last layer of the candidate neural network model, $p_i$ denotes an actual probability distribution corresponding to the ECG training data and $\hat{p}_i$ denotes a probability distribution estimated using the candidate neural network model.

20. A electrocardiogram (ECG) authentication device comprising:
an antenna;
a cellular radio configured to transmit and receive data via the antenna according to a cellular communications standard;
a touch-sensitive display;
a sensor configured to measure an ECG signal of a subject;
a memory configured to store instructions; and
a band pass filter to filter the ECG signal;
a processor configured to receive the ECG signal, to extract a semantic feature of the ECG signal using a neural network model, to authenticate the subject based on the extracted semantic feature, and to display the result of the authenticate on the touch-sensitive display, wherein the neural network model is trained by detecting a fiducial point from the ECG signal after filtering and using a candidate neural network model selected from candidate neural network models whose cross-entropy of its uppermost layer has been minimized; and
acquiring a data segment from the filtered ECG signal based on the fiducial point.

* * * * *